(12) United States Patent
Olivier et al.

(10) Patent No.: US 6,245,918 B1
(45) Date of Patent: Jun. 12, 2001

(54) PREPARATION OF A MOLTEN SALT FROM TRIALKYLOXONIUM ANION AND AMINE

(75) Inventors: Hélène Olivier, Rueil Malmaison; Frédéric Favre, Paris, both of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/322,924

(22) Filed: Jun. 1, 1999

(30) Foreign Application Priority Data

May 29, 1998 (FR) .................................................. 98/06790

(51) Int. Cl.[7] ...................... C07D 233/56; C07D 233/58; C07D 213/06
(52) U.S. Cl. .................. 548/335.1; 546/348; 546/349
(58) Field of Search .......................... 548/335.1; 546/348, 546/349

(56) References Cited

FOREIGN PATENT DOCUMENTS

| 0 404 179 | 12/1990 | (EP) . |
| 0 748 653 | 12/1996 | (EP) . |
| 0 748 785 | 12/1996 | (EP) . |
| 2 684 375 | 6/1993 | (FR) . |
| 98/06106 | 2/1998 | (WO) . |

*Primary Examiner*—Floyd D. Higel
(74) *Attorney, Agent, or Firm*—Millen, White, Zelano & Branigan, P.C.

(57) ABSTRACT

Process for the preparation of an ionic compound, $Q^+A^-$ liquid at less than 150° C., wherein a trialkyloxonium of the anion is reacted with an amine in a hydrocarbon solvent. The aforesaid ionic compound can be used as a solvent in numerous catalytic reactions.

20 Claims, No Drawings

PREPARATION OF A MOLTEN SALT FROM TRIALKYLOXONIUM ANION AND AMINE

The present invention relates to a process for preparing an ionic compound $Q^+A^-$, which is a liquid at low temperature, by reacting a trialkyloxonium of the anion and an amine, in a hydrocarbon solvent, and to its use.

Said compound forms part of non aqueous ionic media, also known as molten salts, which are organic/inorganic slats with general formula $Q^+A^-$, wherein $Q^+$ represents a quaternary ammonium ion and $A^-$ represents an anion which is known to be non coordinating and capable of forming a liquid salt at low temperatures, such as, as is preferable, tetrafluoroborate, hexafluoroborate, hexafluoroantimonate, hexafluoroarsenate and tetrachloroaluminate anions. The quaternary ammonium cations are preferably imidazolium and pyridinium, such as 1-methyl-3-butylimidazolium, 1-ethyl-1-butylimidazolium or N-butylpyridinium. These media can be used as solvents in catalytic reactions.

Different methods for preparing these salts are known. As an example, in J. Chem. Comm. 965 (1992). Wilkes describes a synthesis method starting from silver salts such as acetates, tetrafluoroborates, nitrates, sulphates and 1-ethyl-3-methylimidazolium chloride in a water-methanol mixture as the solvent. The silver chloride is filtered at the end of the reaction and the solvent is evaporated off under vacuum.

Further, in International patent WO 96/18459, a more economical process has been described wherein lead salts are reacted with acetate, fluoroborate, nitrate and sulphate anions with pyridinium, imidazolium and phosphonium chlorides in the same water-methanol solvent.

However, for use as solvents for Diels-Alder reactions and reactions catalyzed by transition metals such as hydrogenation, hydroformylation, isomerization of the double bond in the olefin, the presence of residual chloride ions or traces of water in the molten salts can have a deleterious effect on the catalytic activity of the system. One means which is usually used to eliminate practically all of the chloride ions is to wash the salt with water when the salt is not miscible with water.

The preparation methods described above have the disadvantage of resulting in ionic media from which it is difficult to eliminate traces of unreacted chloride ions and traces of water. This is particularly the case for salts which are miscible with water, for example tetrafluoroborate salts such as those of 1-methyl-3-butylimidazolium tetrafluoroborate for which the unreacted dialkylimidazolium chloride cannot be eliminated by washing with water.

It has now been discovered that it is possible to use in these processes these salts which are liquid at low temperature, i.e., below 150° C., or even below 120° C., advantageously below 90° C., and preferably at most 85° C., and at most 50° C. synthesized in the absence of free chloride ion by reacting the trialkyloxonium of the anion with an amine in a hydrocarbon solvent. The reaction is advantageously carried out in the absence of water or in the presence of small quantities of water supplied, for example, by the solvent.

A further advantage of the present invention is that the only by-product formed during the preparation is a volatile ether which is readily separable from the salt by vacuum evaporation.

The amines of the invention preferably have general formulae $NR^1R^2R^3$ (I) or general formulae $R^1N=CR^2R^3$ (II), where $R^1$, $R^2$ and $R^3$, which may be identical or different, represent hydrogen with the exception of ammonia, and preferably a single substituent represents hydrogen, or hydrocarbyl residues containing 1 to 12 carbon atoms, for example saturated or unsaturated, cycloalkyl or aromatic, aryl or aralkyl alkyl groups containing 1 to 12 carbon atoms. The amines can also be derivatives of nitrogen-containing heterocycles containing 1, 2 or 3 nitrogen atoms with general formulae (III) and (IV):

where the cycles are constituted by 4 to 10 atoms, preferably 5 to 6 atoms, $R^1$ being as defined above.

The amines can have the following formula:

$$R^1N=CR^2—R^4—R^2C=NR^1 \quad (V)$$

where $R^1$ and $R^2$, which may be identical or different, are as defined above and $R^4$ represents as alkylene or phenylene residue. Examples of groups $R^1$ and $R^2$ are methyl, ethyl, propyl, isopropyl, butyl, secondary butyl, tertiary butyl, amyl, methylene, ethylidene, phenyl or benzyl radicals; $R^4$ can be a methylene, ethylene, propylene or phenylene group.

The amine is preferably selected from the group formed by pyridine, 1-methylimidazole, 1-ethylpyrazole, 1-ethylimidazole, 1-butylimidazole and 1,2-dimethylimidazole.

The trialkyloxonium of the anion is selected from the group formed by the trimethyloxonium and the triethyloxonium of the anion.

The hydrocarbon solvent used in the invention is preferably non miscible with the ionic medium formed. Advantageously, a polar solvent is used. It contains no or only a little water. Examples are 1,2-dichloroethane, dichloromethane, and 1,1,1-trichloroethane.

The temperature at which the reaction is carried out is in the range 50° C. to 200° C.; advantageously the temperature is less than 150° C. and advantageously less than 90° C. and will remain below the decomposition temperature of the reactants.

The molar ratio between the trialkoxonium of the anion and the amine is in the range 0.5 to 3, preferably in the range 0.9 to 2.

EXAMPLES

The following examples illustrate the invention without limiting its scope:

Example 1

Preparation of the Salt of 1-methyl-3-ethylimidazolium Tetrafluoroborate 22.3 ml of N-methylimidazole and 120 ml of 1,2-dichloroethane were introduced into a 250 ml glass flask under an argon atmosphere. 53.2 g of triethyloxonium tetrafluoroborate was added in small portions. The reaction medium was observed to heat up slightly and the solvent was then refluxed for 1 hour 30 minutes. The molten salt formed was colorless, non miscible and denser than the 1,2-dichloroethane. It was separated by simple decanting and drawn under vacuum using a vane pump.

Example 2

Preparation of the Salt of 1-butyl-3-ethylimidazolium Hexafluorophosphate 1.1 ml of N-butylimidazole was introduced into a 50 ml glass flask under an argon atmosphere. 2.08 g of triethyloxonium hexafluorophosphate in solution in 5 ml of 1,2-dichloroethane was then introduced. The mixture was stirred for 4 hours at room temperature. The solvent was evaporated off under vacuum using a vane pump. A colorless liquid was obtained.

Example 3

Preparation of the Salt of 1,3-dimethylimidazolium Tetrafluoroborate

The procedure of Example 2 was followed. 3.9 g of trimethyloxonium tetrafluoroborate in suspension in 20 ml of 1,2-dichloroethane was added to 2.1 ml (2.16 g) of N-methylimidazole in 5 ml of 1,2-dichloroethane. The mixture was stirred for 4 hours at room temperature. A salt was formed (lower phase) which was non miscible with the solvent and was separated by decanting. The remaining solvent was evaporated off under vacuum using a vane pump. A colorless liquid was obtained.

Example 4

Preparation of the Salt of 1-methyl-3-butylimidazolium Tetrafluoroborate

The procedure of Example 2 was followed. 3 g of trimethyloxonium tetrafluoroborate in suspension in 10 ml of 1,2-dichloroethane was added to 2.7 ml of N-butylimidazole in 10 ml of 1,2-dichloroethane. The mixture was stirred for 4 hours at room temperature. The remaining solvent was evaporated off under vacuum using a vane pump. A colorless liquid was obtained.

What is claimed is:

1. A Diels-Alder reaction or a reaction catalyzed by a transition metal, conducted in a non aqueous ionic solvent $Q^+A^-$, which is a liquid below 150° C., wherein $Q^+$ is a quaternary ammonium ion and $A^-$ is a non-coordinating anion, $Q^+A^+$ being prepared by reacting a trialkyloxonium of $A^-$ with an amine in a hydrocarbon solvent.

2. A process according to claim 1 in which anion $A^-$ is tetrafluoroborate, hexafluorophosphate, hexafluoroantimonate, hexafluoroarsenate or tetrachloroaluminate.

3. A process according to claim 1 in which $Q^+A^-$ is liquid at a temperature of less than 120° C.

4. A process according to claim 1 in which $Q^+A^-$ is a liquid at a temperature of less than 90° C.

5. A process according to claim 1 in which $Q^+A^-$ is liquid at a temperature of less than 50° C.

6. A process according to claim 1, in which the amine has the following formula:

$$NR^1R^2R^3 \quad (I)$$

$$R^1N=CR^2R^3 \quad (II)$$

where $R^1$, $R^2$ and $R^3$, which may be identical or different, represent hydrogen with the exception that (I) does not represent ammonia, or a $C_{1-12}$-hydrocarbon.

7. A process according to claim 1 in which the amine is a nitrogen-containing heterocyclic compound containing 1, 2 or 3 nitrogen atoms of the formulae:

where

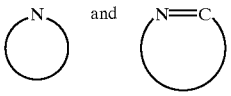

represent heterocyclic rings of 4 to 10 atoms, and $R^1$ represents a $C_{1-12}$-hydrocarbon or hydrogen.

8. A process according to claim 1 in which the amine is of the formula:

$$R^1N=CR^2—R^4—R^2C=NR^1 \quad (V)$$

where $R^1$ and $R^2$, which may be identical or different, represent a $C_{1-12}$ hydrocarbon or hydrogen, and $R^4$ represents alkylene or phenylene.

9. A process according to claim 6, in which $R^1$, $R^2$, $R^3$ are saturated or unsaturated, cycloalkyl or aromatic, aryl or aralkyl alkyl groups containing 1 to 12 carbon atoms.

10. A process according to claim 6, in which $R^1$, $R^2$ and $R^3$ are methyl, ethyl, propyl, isopropyl, butyl, secondary butyl, tertiary butyl, amyl, methylene, ethylidene, phenyl or benzyl.

11. A process according to claim 8, in which $R^4$ is methylene, ethylene, propylene or phenylene.

12. A process according to claim 1 in which the amine is pyridine, imidazole, 4-methylpyrazole, 1-methylpyrazole, 1-methylimidazole, 1,2-dimethylimidazole, 1-ethylimidazole or butylimidazole.

13. A process according to claim 1 in which the hydrocarbon solvent is non-miscible with $Q^+A^-$.

14. A process according to claim 1 in which the hydrocarbon solvent is 1,2-dichloroethane, 1,1,1-trichloroethane, dichloromethane or acetonitrile.

15. A process according to claim 1 in which the trialkyloxonium of $A^-$ is triethyloxonium of $A^-$ or trimethyloxonium of $A^-$.

16. A process for catalytic hydrogenation, hydroformylation, or isomerization of an olefinic double bond, comprising subjecting a hydrocarbon feed to hydrogenation, hydroformylation or isomerization conditions in contact with a catalyst comprising a non-aqueous solvent of formula $Q^+A^-$ which is a liquid at a temperature of less than 150° C., wherein $Q^+$ is a quaternary ammonium ion and $A^-$ is a non-coordinating anion, $Q^+A^-$ being prepared by reacting a trialkyloxonium of $A^+$ with an amine in a hydrocarbon solvent.

17. A process according to claim 6, wherein only one of $R^1$, $R^2$ and $R^3$ represents hydrogen.

18. A process according to claim 8, wherein only one of $R^1$, $R^2$ and $R^3$ represents hydrogen.

19. A process according to claim 1 in which anion $A^-$ is a hexafluorophosphate, hexafluoroantimonate, hexafluoroarsenate or tetrachloroaluminate.

20. A process according to claim 1 in which anion $A^-$ is hexafluorophosphate, hexafluoroantimonate, hexafluoroarsenate or tetrachloroaluminate or hexafluorophosphate.

* * * * *